United States Patent [19]
Schoen

[11] Patent Number: 4,570,103
[45] Date of Patent: Feb. 11, 1986

[54] PARTICLE BEAM ACCELERATORS

[76] Inventor: Neil C. Schoen, 13 Golden Star, Irvine, Calif. 92714

[21] Appl. No.: 430,285

[22] Filed: Sep. 30, 1982

[51] Int. Cl.[4] .............................................. H01J 25/10
[52] U.S. Cl. ..................................... 315/5.41; 372/2; 315/4; 315/5.42; 328/233
[58] Field of Search ....................... 372/2; 315/3, 4, 5, 315/5.41, 5.42; 328/233

[56] References Cited

U.S. PATENT DOCUMENTS

| | | | |
|---|---|---|---|
| 3,267,383 | 8/1966 | Lohmann | 315/4 |
| 3,450,931 | 6/1969 | Feinstein et al. | 315/5 |
| 4,463,959 | 8/1969 | Jory et al. | 315/5 |
| 3,622,833 | 11/1971 | Takeda et al. | 315/4 |
| 3,730,979 | 5/1973 | Schwarz et al. | 315/4 |
| 3,860,880 | 1/1975 | Yariv et al. | 315/4 |
| 4,215,291 | 7/1980 | Friedman | 315/4 |

OTHER PUBLICATIONS

*IEEE Transaction on Nuclear Science,* vol. NS-28, No. 3, 6/81, "An Experiment on FEL Efficiency Enhancement with a Variable Wiggler," by H. Boehmer et al.

*Primary Examiner*—Saxfield Chatmon

[57] ABSTRACT

A technique for accelerating charged particles using an intense traveling electromagnetic wave such as produced by appropriate wavelength lasers. Low energy electrons injected into the focal region of an intense, polarized laser beam are rapidly accelerated in the direction of the beam by the ponderomotive force of the radiation field. The particles reach maximum energy in a distance comparable to the Rayleigh range of a tightly focussed, visible wavelength, diffraction limited pulsed laser. At this point, a combination of induced transverse velocity drifts and/or the rapidly decreasing electric field strengths due to the expanding laser beam envelope cause the particles to enter a low radiation field region before significant deceleration can occur. The resulting device possesses unique advantages and properties not present in existing accelerators.

9 Claims, 6 Drawing Figures

NOT TO SCALE

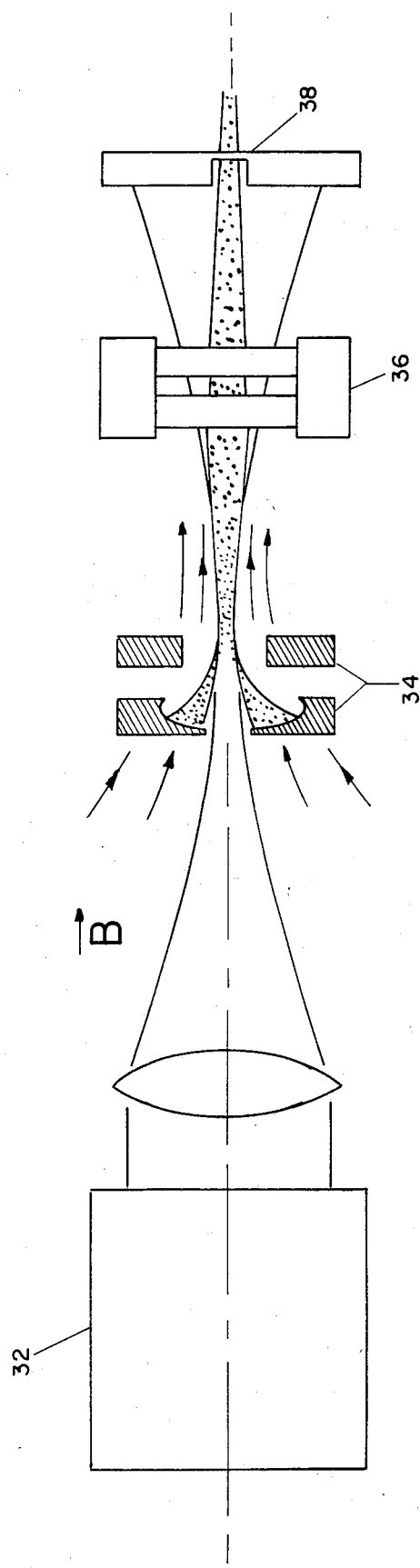

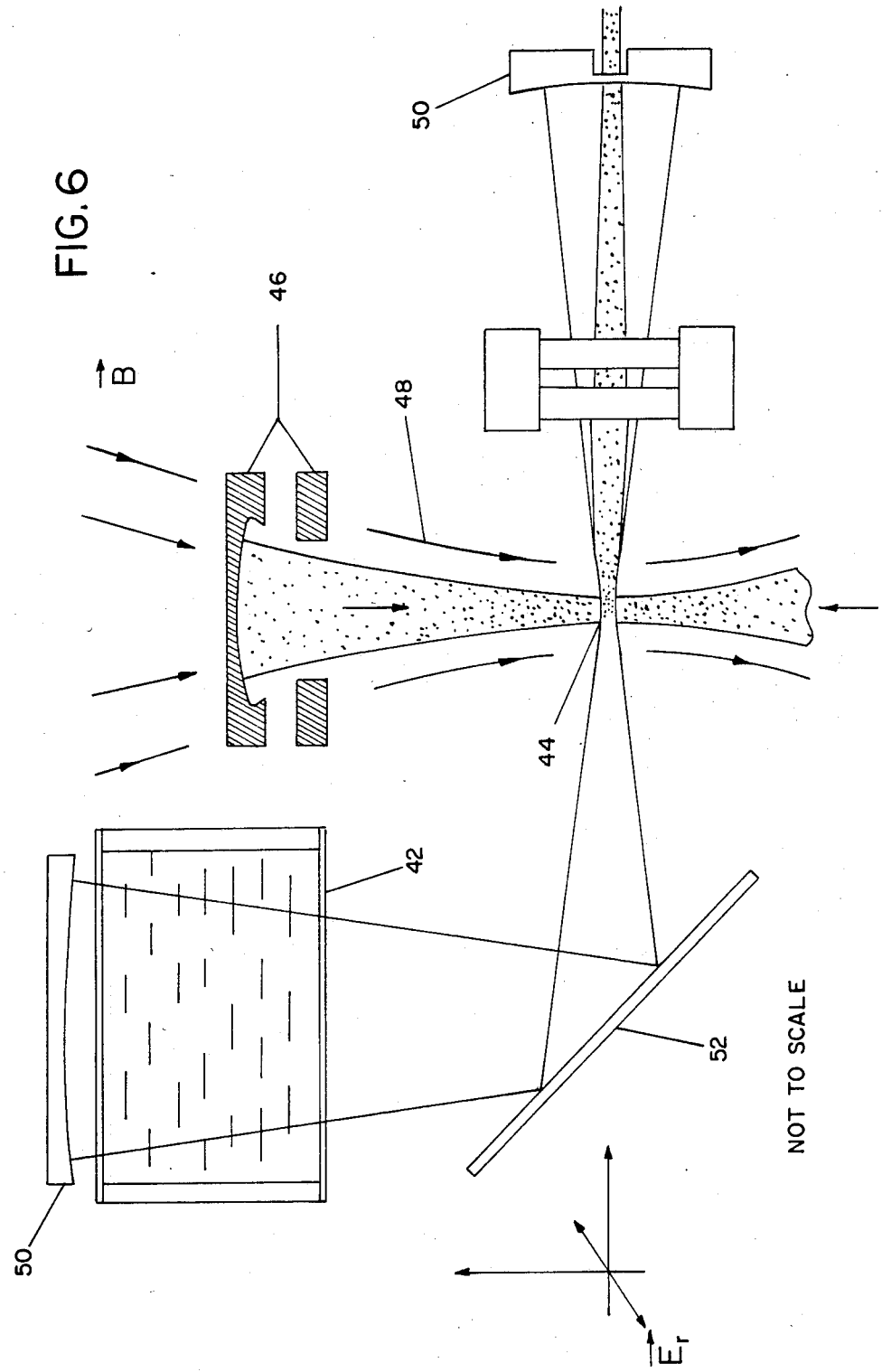

PARTICLE BEAM ACCELERATORS

INTRODUCTION

The need for high energy, high current particle accelerators is rapidly growing due to a number of significant applications for this technology. Such practical uses include particle beam weapon systems, medical devices for cancer treatment, and plasma heating for fusion energy systems. Although particle accelerators have existed for over fifty years, the combination of high energy and high current has been difficult to achieve with present technology. The following brief summary of conventional and advanced acceleration techniques will serve to clarify the unique properties of the present invention.

Present day accelerators are generally divided into linear or circular categories, although the actual acceleration method is common to both types. Linear accelerators (LINACS) tend to be simpler in construction, requiring no magnetic fields to bend the particles, although newer devices have electric or magnetic focusing elements to counteract space charge forces, which tend to enlarge the beam. Typical LINACS require high power radio frequency (RF) inputs and resonant cavities to deliver a properly phased electric field across sequential accelerating gaps. As particles accelerate, those of the proper phase relative to the RF always reach an accelerating gap when the field in the gap is at a peak and thus receive the maximum acceleration possible. Thus, only a certain fraction (or phase bucket) of particles is accelerated from the stream of input particles, creating a duty cycle factor effect. This can be overcome to some degree by pre-bunching the particles before injection to improve the efficiency of acceleration. High energy LINACS tend to be long (up to 2 miles for 20 GeV electrons) and expensive. Current is limited in LINACS due to particle/cavity interaction modes, which causes cavity loading and beam instabilities, as well as by space charge forces which tend to "blow up" the beam.

Circular accelerators tend to be more compact, but require very high DC magnetic fields to confine the high energy particles. Oscillation of the accelerated beam in the bending and focusing magnetic fields is also a cause of beam "blow up" and instability which limits the currents achievable in typical circular devices such as cyclotrons, betatrons, synchrotrons, and other periodic systems. For particles such as electrons, radiation power losses become significant in circular devices at high energies, limiting their effectiveness.

It should be noted that both linear and circular accelerators require high power RF and cavity structures to create electric fields parallel to the velocity vector of the accelerating particles.

The present invention utilizes a traveling electromagnetic wave to accelerate particles. No cavities or external magnetic fields are necessary as in existing devices or conceptual models representing the state of the art. Depending on the state of the art in laser development, this device can be extremely compact, since acceleration is produced in a single step in a region of very small spatial extent. The particles are accelerated by the electric vector of the polarized traveling wave, which is transverse to the laser beam axis and the direction of major acceleration. As soon as the particles achieve significant transverse velocity, they interact with the magnetic vector of the laser beam and are thus deflected in the direction of the beam by this ponderomotive force. This device is thus a "transverse" accelerator in principle as compared with the tangential or linear acceleration of conventional devices. Because of the very high electric and magnetic fields involved in the acceleration process and the small spatial acceleration region, space charge forces and other instabilities should be relatively insignificant in limiting achievable instantaneous particle currents thus allowing high peak power outputs.

SUMMARY OF THE INVENTION

An implementation of the present invention is accomplished as follows. A region of very intense electromagnetic radiation is created by focusing a high power, pulsed laser beam to a near diffraction limited spot. If the laser optics are such that the f-number (focal length divided by aperture) is near one, then diffraction limited spot sizes can approach the size of the wavelength of light produced by the laser. For the shorter wavelength visible region of the spectrum, submicron size beams are feasible and thus very high peak power can be obtained with modest laser power due to the very small region within which all the energy is concentrated. If the laser radiation is circularly polarized, one now has an intense traveling electromagnetic wave (circularly polarized TEM mode) in a highly confined spatial region, which exists for the length of time of the laser pulse, and is suitable for accelerating charged particles to high energies by virtue of the very large electric field strengths present at the focal region. The acceleration mechanism is as follows.

Particles are injected into the high field strength focal region. Consider, for example, an electron (with charge $-e$) present with low initial energy in the strong traveling wave field. The electron is initially accelerated in the direction of the electric field vector $\bar{E}_\gamma$ of the beam, which is transverse to the optic axis of the laser beam. When the electric field magnitude is very large, the electron acquires a significant transverse velocity component before the electric field vector rotates significantly due to the circularly polarized nature of the radiation. This transverse velocity vector $\bar{v}_\perp$ then interacts with the almost orthogonal magnetic field vector $\bar{B}_r$ according to the well known ponderomotive force law $e\bar{v}_\perp \times \bar{B}_\gamma$. This force gives the electron a velocity kick in the axial direction of the traveling wave. As the electric field vector rotates the electron transverse velocity vector $\bar{V}_\perp$ tends to follow the rotating electric field $\bar{E}_\gamma$. If the electron axial velocity reached the speed of light $c$ (i.e. $\beta_\| = |v_\||/c = 1$), then the electron and traveling wave would be in perfect synchronism and the acceleration process would continue indefinitely. Because the electron can never travel at the velocity of the electromagnetic wave, the electron transverse velocity vector $\bar{v}_\perp$ eventually slips out of phase with the electric field vector $\bar{E}_\gamma$ and eventually the transverse velocity vector and electric field are in opposition and deceleration occurs. If the intensity of the electromagnetic wave is too low at the focal region, the electron never attains an axial velocity sufficient to remain in near synchronism and thus never achieves high energies at any time.

A key feature of the present invention is the techniques for extracting the accelerated particles from the high field region so that deceleration does not occur. There are two injection techniques which will achieve this desired extraction process. One method is to inject particles transverse to the laser beam direction at the focal plane. The injection velocity can be adjusted so that the particles drift through the focal waist or high field region in a time necessary to reach peak energy. A second method is to inject the particles in an axial direction prior to the focal plane. As the particles drift in the direction of the laser beam, they enter the high field focal region and are accelerated. If the Rayleigh length of the beam is adjusted to match the acceleration length appropriate to the attainable electric field strengths, then the accelerated particles experience rapidly dropping electric field strengths as they enter the deceleration phase, thus limiting the deceleration process. There is also an added benefit to axial injection, in that the particles reach higher peak energies with modest axial injection velocities ($\beta_\parallel < 0.9$).

With regard to the features of this invention which distinguish it from prior art, the most significant is the compact nature of the acceleration region. Conventional accelerators require large structures to sustain the accelerating electric fields and typically achieve acceleration levels of approximately 1 MeV per meter. With suitable power laser drivers, the present device should allow two or three orders of magnitude improvement in this figure of merit. In addition, this acceleration mechanism should be relatively insensitive to space charge effects since the acceleration takes place in a very localized spatial region where the acceleration fields will dominate over the space charge fields. Limitations on the maximum currents achievable with this device should depend only on how much charge can be placed in the focal region and the levels at which the fields became depleted due to the loading or loss from the acceleration process. The following detailed descriptions of the potential modes of operation of this device will further serve to illustrate the advantageous features of the present invention and the unique aspects which distinguish it from presently existing devices and speculations about future accelerators.

DESCRIPTION OF THE DRAWINGS

FIG. 5 is a schematic diagram of a laser driven accelerator constructed in accordance with the present invention;

FIG. 6 is a schematic diagram illustrating possible alternate configurations utilizing a focal plane internal to the laser resonator and transverse electron injection.

DESCRIPTION OF PREFERRED EMBODIMENTS

The principles on which the present invention rests indicate that this device will operate effectively when the traveling electromagnetic wave lies in the radio-frequency to ultraviolet spectral range. For purposes of explanation and clarification, devices configured to operate with visible or microwave radiation and which utilize lasers or maser-type microwave sources are described. This should not be construed as to limit the scope of this invention in any way or fashion to a particular spectral region or source, nor should the particular configurations to be described limit the potential embodiments of said invention.

The unique and special properties germane to this invention were developed with the aid of a computer code written by the inventor, and the results of these computer calculations are presented herein to support claims and embodiments to be described.

Figure 1:
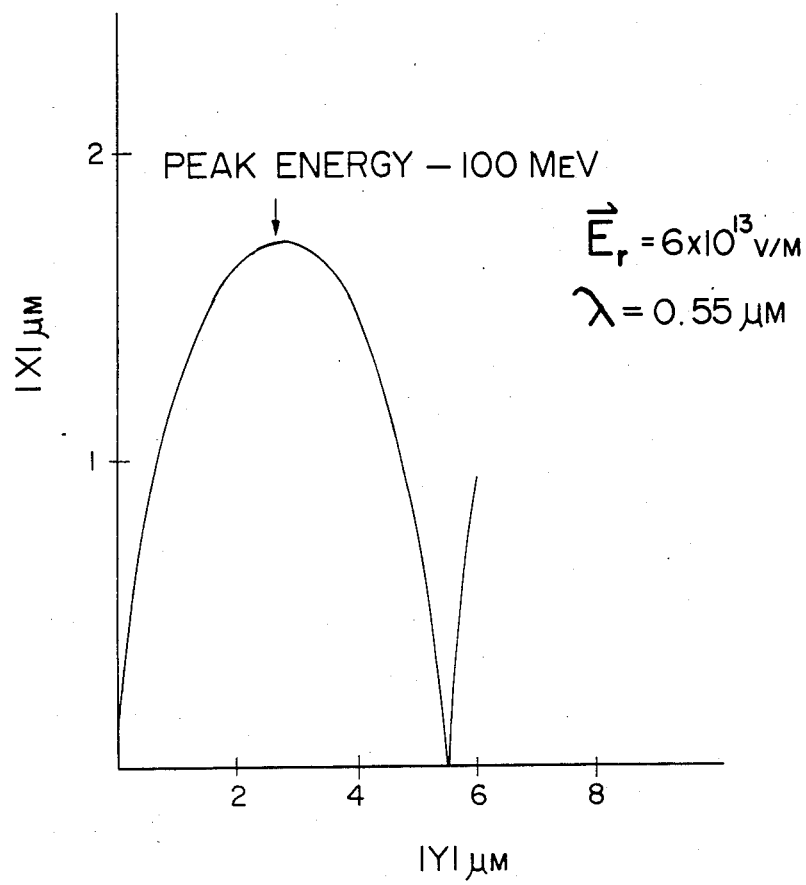
FIG. 1 is a graph showing the orbit of an electron under the influence of an intense circularly polarized traveling wave.
Figure 1:
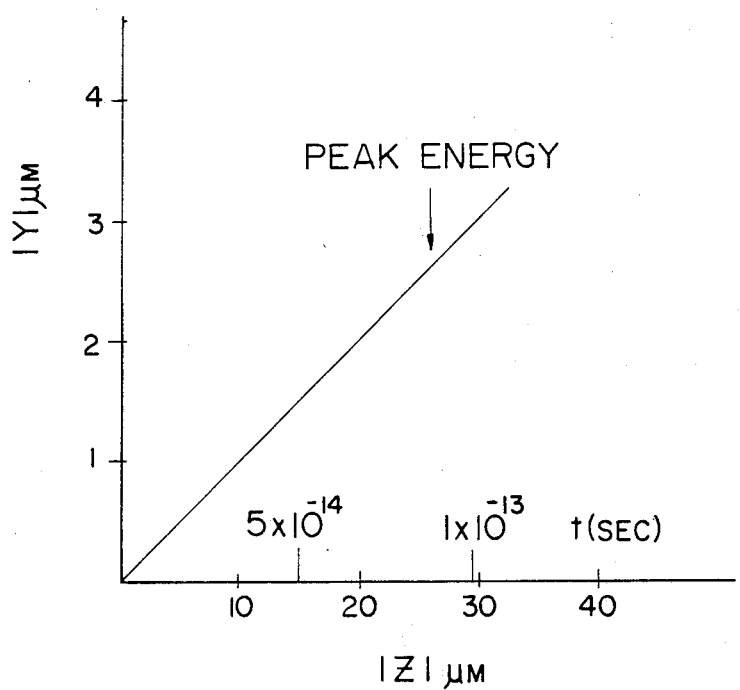

The orbital motion of an electron in a circularly polarized plane wave of high electric field strength is shown in FIG. 1. The particle is initially at rest and the wave fields are "turned on" at $t=0$ to full strength, an idealized case chosen to illustrate the fundamentals of operation. An electric field strength of $6 \times 10^{13}$ volts/meter and a wavelength of about 0.55 microns was used for this simulation. The electron reaches a peak energy of about 100 MeV in about $10^{-13}$ seconds before the phase slippage causes a deceleration to begin. The electron travels in the direction of the wave about 30 microns before reaching peak energy. The electron oscillates in the $-x$ direction but acquires a constant drift velocity in the y direction as a result of the initial phase of the wave at $t=0$. This induced drift can play an important part in preventing deceleration from occurring in certain configurations.

The Rayleigh length of a beam is defined as the distance from a beam waist in which the area of the beam has increased by two. The Rayleigh length $L_R$ can be written as $$L_R = \frac{\pi a^2}{\lambda}$$

where a is the radius of the waist. The waist can be as small as the quantity $\sim f^\# \lambda$ according to diffraction theory, where $f^\#$ is the f-number of the optics and is usually $>1$. If we choose a near diffraction limited waist of about $a=2$ $\mu$m, then the region of significant field strength (i.e. $>\frac{1}{2}$maximum) is $2L_R$ which for 0.55 $\mu$m radiation approaches 45 $\mu$m. This is comparable to the region of maximum acceleration and therefore represents a natural mechanism for preventing deceleration of the particles after they have reached peak energy. This feature is a unique aspect of the present invention which makes practical acceleration systems possible.

Figure 2:
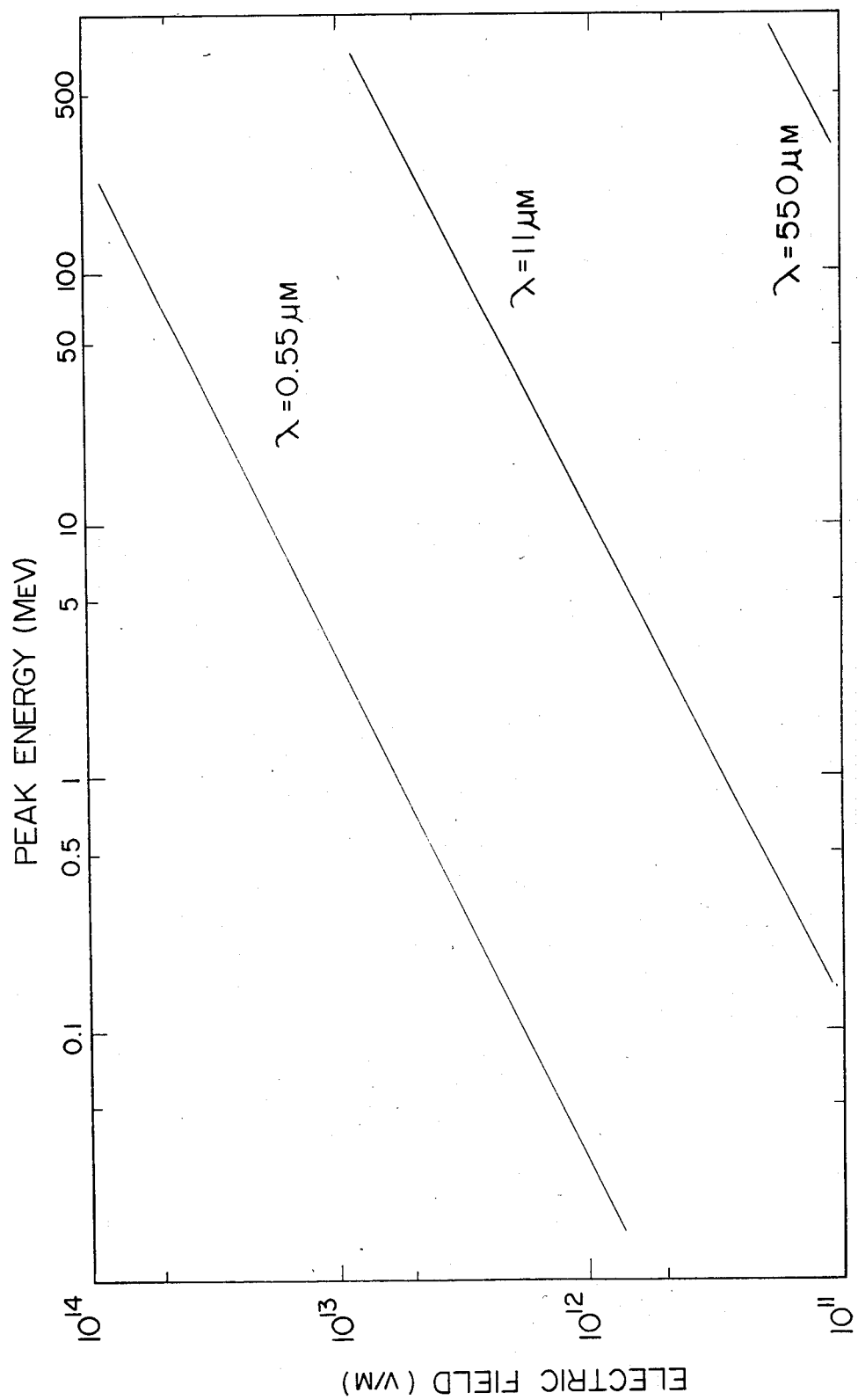
FIG. 2 is a graph showing the peak evergy levels reached by electrons accelerated by uniformly intense beams of varying electric field strengths.

The magnitude of attainable peak electron energies with various wavelength sources and power densities is shown in FIG. 2. The scaling laws are as follows. For a fixed wavelength, the peak energy scales as the square of the electric field strength, which is to be expected on elementary grounds. If one chooses a given peak acceleration level, then the electric field strength necessary to achieve that energy is inversely proportional to the wavelength (i.e. $E_\gamma \alpha 1/\lambda$).

If one has a fixed electric field strength, then the peak energy attainable for electrons is proportional to the square of the wavelength (i.e. $MeV \alpha \lambda^2$). If one assumes that the minimum waist size is proportional to $\lambda$ by diffraction theory, then the peak energy levels attainable will not depend on the wavelength, and selection of the optimum wavelength source will depend on other factors such as available laser power, maximum acceleration currents, device size, cost, etc.

Figure 3:
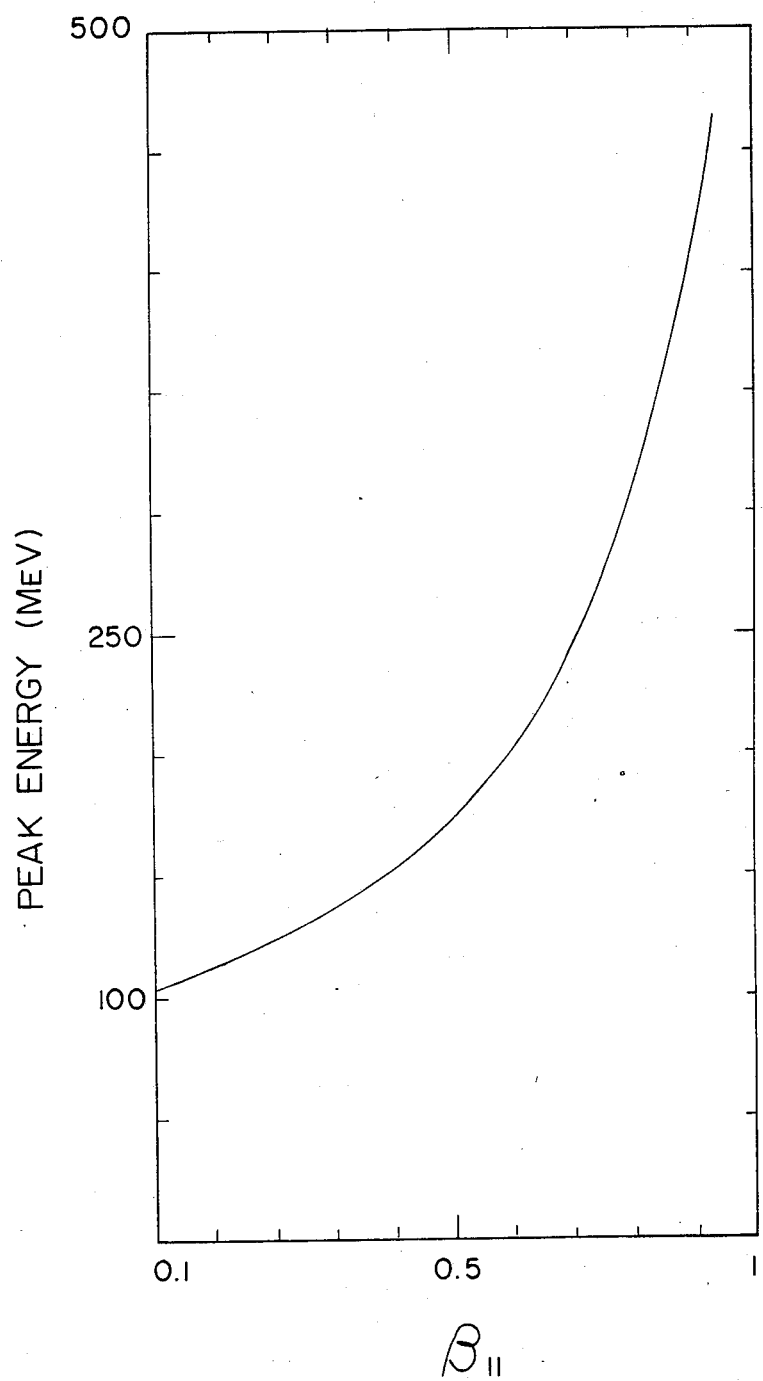
FIG. 3 is a graph showing the increase in peak electron energy levels as the initial injection velocity of the electrons in the axial direction is increased.

One of the distinct advantages of the present invention is the lack of restrictions on the particle injection process. For the case of electrons, the most likely production mechanism is a field emission diode which can provide very high electron densities in small regions. Particles can be accelerated regardless of the initial velocity states, as has been demonstrated by a sensitivity analysis using the particle orbit code. This is in contrast to present devices where particle velocity and radiation phase are critical to the capture and acceleration process. There is some advantage to axial injection if it is done in the focal plane, since the increased axial velocity of the electron allows it to stay in phase with the electromagnetic traveling wave for a longer time. This can be seen in FIG. 3 for a uniform $0.55\mu$ plane wave at $6 \times 10^{13}$ volts/meter. The increase in the peak electron energy as the initial electron velocity parallel to the optic axis increases can seem to be significant. It thus appears that injection with axial velocity levels near $\beta_\| \cong 0.9$ is desirable. Since most field emission devices operate at several hundred kilovolts, this does not pose additional power requirements.

Figure 4:
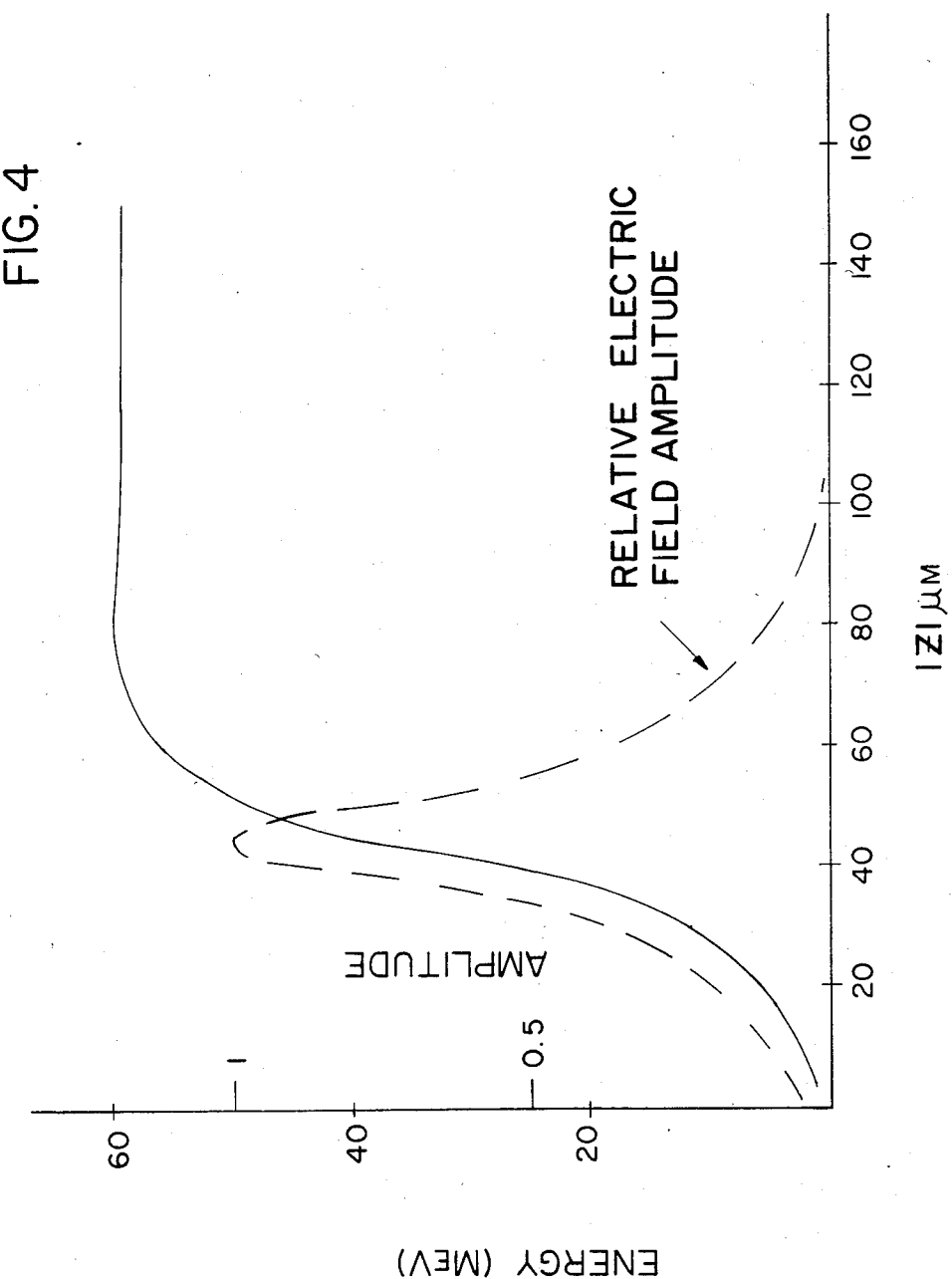
FIG. 4 is a graph showing how electrons retain the energy they have gained when the Rayleigh length of the laser beam is properly adjusted to the region of maximum acceleration.

All of the previously described results were based on the assumption of a constant amplitude, plane phase TEM wave. In the Rayleigh focal region of a focused laser beam, the field has limited transverse extent and the phase front of the wave has curvature to it at the extremes of the Rayleigh range as it transitions to an ingoing or outgoing spherical wave. This means that the electric field vector of the wave varies with axial position (along the optic axis) as well as with transverse position. To determine the additional effects of these spatial variations in the laser beam, a simple model was used which incorporated amplitude variations in the electric field strength in both the transverse and axial directions. The results of these computer simulations are shown in FIG. 4. Note that the particle is accelerated in the high field Rayleigh region as before, but retains nearly all its energy as it drifts into the lower field region. The fact that one can tailor the Rayleigh range to prevent significant deceleration is a key feature of the present invention, since injection velocities are not critical to the prevention of the deceleration process.

With regard to the existence of prior art, it should be noted that no practical high energy accelerators using the principles of this invention exist as of this date, nor are any under construction. This device is quite clearly distinct from conventional acceleration methods. In the matter of speculation in the literature regarding potential future particle acceleration techniques, there has been some awareness of the possibility of using traveling electromagnetic waves for acceleration purposes. One recent scheme, in which the present inventor has been involved, utilizes a TEM wave in conjunction with a solenoidal or axial magnetic field. In this arrangement, the particles can stay in phase with the electric field indefinitely, provided the particles are injected properly. The major disadvantages of this approach are the high solenoidal magnetic fields required and the sensitivity of the acceleration mechanism to small excursions from resonant or synchronous conditions. The only speculations regarding particle acceleration by free-standing traveling waves dealt with the possibility of this mechanism being operative on a cosmological scale, i.e. in super-novas, etc. No attempt to solve the problem of deceleration was attempted, nor was any configuration for a practical device postulated.

A preferred embodiment of the present invention is shown in FIG. 5. A high power pulsed laser 32 is brought to a near diffraction limited focal spot, which serves as the acceleration region due to the presence of high field strengths in the Rayleigh region of the focal plane. An intense electron source 34 such as provided by field emission diodes or pulsed plasma sources, is located coaxially with the laser beam. The electron source should be optimally focused to provide the maximum number of electrons in the acceleration volume bounded by the laser beam envelope in the Rayleigh region. The electrons are injected with axial velocities approaching $\beta_\| < 0.9$. This serves to feed particles into the acceleration region as well as provide enhanced acceleration, as illustrated in FIG. 4. The accelerated particles will emerge from the acceleration region in a conical beam due to induced transverse velocities and thus may require some magnetic quadrupole devices 36 to properly control the beam. The accelerated electrons then pass through a thin vacuum window 38 which also serves as a laser beam disperser or dump.

Another injection method, utilizing a transverse feed, has some distinct advantages compared with coaxial injection. Transverse injection utilizes an electron stream that is directed normal to the laser beam axis. The beam must be linearly polarized for transverse injection to work. This can be as simple as a field emission needle source at the focal plane, or can utilize more complex diodes. Particles must be directed normal to the plane of polarization. Multiple injectors would allow more charge to enter the acceleration region, since overlapping electron beams could create lower restrictions on the quality of the electron source optical system. A transverse injection system may be more immune to particle reflection problems in the converging magnetic field region near the Rayleigh region, since the electron beams can be precisely directed to that location in the Rayleigh region at which maximum acceleration can occur.

An alternate configuration for a laser-driven transverse particle accelerator is shown in FIG. 6. This approach utilizes the higher power densities available inside the resonator of the laser. Power densities could be 10 to 100 times higher within the laser cavity, depending upon the outcoupling fraction utilized in the laser design. The gain medium can be isolated from the vacuum acceleration region by appropriate transparent windows 42. A transverse injection system is used 44, which is normal to the plane of polarization of the linearly polarized beam as is shown in the inset. Two field emission diodes 46 are magnetically focussed 48 on to the Rayleigh region. The laser resonator cavity mirror 50 and a folding mirror (for alignment stability) 52 are also depicted. The addition of some axial velocity will favor acceleration by one of the two traveling waves.

There are other configurations for accelerators based on the principles of this invention. One such embodiment consists of periodically refocussing the traveling wave and electron beam, thereby creating periodic acceleration regions which allow higher energies to be reached. These regions can be as compact as the magnetic design will allow, since the optical constraints will be less severe than the electron beam focusing requirements. If the system is designed to operate in the microwave region, the electron focal problems will be less severe, since the microwave acceleration region will be of much larger cross section due to the longer wavelength of the radiation. Microwave refocussing might be accomplished via undulations in the waveguide cross sections or dielectric lens, if power levels permit.

The principles set forth in the present invention allow for many variations in the design of practical devices, and they are implicitly claimed as part of the full embodiment of this invention.

Specifically, what is claimed is as follows:

1. An apparatus for the acceleration of charged particles comprising a source radiation beam of intense coherent polarized traveling electromagnetic waves, means bringing said radiation beams or waves to a near-diffraction limited focal region, with said near-diffraction limited focal region created by an optical or quasi-optical radiation resonator operating in a TEM mode, whereupon a charged particle stream or streams caused to be present at said focal region is accelerated to high energies by the electric field vector of said traveling wave, which is transverse to the direction of propagation of said radiation beam, thereby causing said charged particles to achieve significant transverse velocity, causing them to then interact with the magnetic field vector of said radiation beam via a v×B ponderomotive force, thereby deflecting said charged particles in the direction of said propagating radiation beam and causing the transverse velocity vectors of said charged particles to remain in near synchronism with the electric field vector of said traveling wave and thereby continue to gain energy until said charged particles leave said high field focal region.

2. An apparatus according to claim 1 wherein a Rayleigh region and focal spot region are chosen to provide maximum acceleration by iteratively adjusting said focal region to match the region of acceleration, with said region determined by the electric field strengths attainable at the focal plane.

3. A device according to claim 1 wherein the said particle stream is comprised of electrons injected coaxial to a laser beam with velocities approaching the speed of light.

4. A device according to claim 1 wherein the said particle stream or streams is comprised of electrons injected normal to a laser beam with velocities adjusted to produce maximum acceleration.

5. A device according to claim 1 wherein the intense traveling electromagnetic waves are linearly or circularly polarized.

6. An apparatus according to claim 1 wherein said focal region of the traveling electromagnetic waves is internal to the source, such as inside a laser resonator cavity, where power levels are at a maximum.

7. An apparatus to claim 1 wherein the intense traveling electromagnetic waves are periodically refocussed to produce multiple acceleration regions which can act upon previously accelerated particles which are also refocussed, or accelerate newly injected particles to produce multiple beams which may be combined downstream of the accelerator.

8. An apparatus according to claim 1 wherein the source of the intense traveling electromagnetic waves operates in the microwave region, and the required focusing is accomplished via a quasi-optical cavity or dielectric lens array.

9. An apparatus according to claim 1 wherein a solenoidal magnetic field coaxial to the electromagnetic wave is provided to constrain or focus the accelerated charged particles prior to extraction, with said solenoidal magnetic field also serving to extend the length of time the particles remain in near synchronism with the traveling waves, thus allowing higher energies to be attained.

* * * * *